United States Patent [19]

Pedersen et al.

[11] Patent Number: 4,568,783

[45] Date of Patent: Feb. 4, 1986

[54] INDENES BY CATALYTIC DEHYDROGENATION OF INDANES

[75] Inventors: S. Erik Pedersen, Solon; Diane G. Farrington, Brecksville, both of Ohio

[73] Assignee: The Standard Oil Company, Cleveland, Ohio

[21] Appl. No.: 747,739

[22] Filed: Jun. 24, 1985

[51] Int. Cl.$^4$ ............................................. C07C 5/42
[52] U.S. Cl. ................................. 585/442; 585/379; 585/380; 585/445
[58] Field of Search ................ 585/442, 379, 380, 445

[56] References Cited

U.S. PATENT DOCUMENTS

| | | | |
|---|---|---|---|
| 2,392,289 | 1/1946 | McCullough et al. | 585/442 |
| 2,531,328 | 11/1950 | Elwell | 585/445 |
| 3,456,026 | 7/1969 | Cohen | 585/442 |
| 3,787,517 | 1/1974 | Haag et al. | 585/442 |
| 4,291,180 | 9/1981 | Kiikka | 585/431 |
| 4,291,181 | 9/1981 | Kiikka et al. | 585/320 |
| 4,292,456 | 9/1981 | Kiikka et al. | 585/431 |

Primary Examiner—John Doll
Assistant Examiner—A. Pal
Attorney, Agent, or Firm—Charles S. Lynch; John E. Miller; Larry W. Evans

[57] ABSTRACT

Disclosed is the vapor phase catalytic dehydrogenation of indanes to indenes over a Co—Mo oxide on alumina catalyst and in the presence of sulfur.

4 Claims, No Drawings

INDENES BY CATALYTIC DEHYDROGENATION OF INDANES

This invention relates to a method of dehydrogenating indane or methyl substituted indanes to produce indene or methyl substituted indenes.

Indenes are currently prepared industrially by isolation from coal tar or petroleum distillates. This method yields indene of too low a purity to be useful for preparation of high HDT polymers without extensive and costly purification. High purity indene is not currently an item of commerce in more than research quantities. Syntheses of indene have traditionally relied upon cumbersome, multi-step, non-catalytic methods which are not industrially useful because of their inherently low yields and poor product recovery as well as their requirement of high acidic reaction conditions (see, for example, Wittig, G. *Chem. Ber.* 91, 1958, 895 or Waldman and Schwenk, *Ann.* 487, 1931, 287; or Ulman and Lehner, *Ber.* 38, 1905, 729; or Weedon and Wahler, *J.Am.Chem.Soc.* 33, 1905, 386.

It is an object of the present invention to provide a process for making indenes synthetically.

It is a further object to provide a new method for making indenes by the vapor phase catalytic dehydrogenation of indanes.

It is a still further object to provide a method for the catalytic dehydrogenation of indane or substituted indanes to indene or substituted indenes at high conversion and yields.

Other objects, as well as aspects, features, and advantages, of the invention will be apparent from the disclosure and claims.

These and other objects are realized by the present invention according to which there is provided a process for the catalytic reaction of sulfur and an indane compound having the formula:

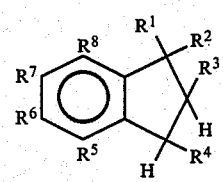

in the vapor phase in the presence of an inert gaseous or vapor diluent to produce:

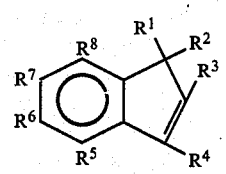

by contacting the reaction mixture with a solid catalyst having 1-10 weight percent CoO, 5-40 weight percent $MoO_3$, the balance of the catalyst being an alumina support, wherein the catalyst contains a Co to Mo ratio in the range from 1/2.5 to 1/6 and wherein the catalyst has a surface area of less than 80 $m^2/gm$, the ratio of atoms of sulfur to moles of indane compound in the feed being in the range from 0.8 to 2, and wherein each of $R^1$, $R^2$, $R^3$, $R^4$, $R^5$, $R^6$, $R^7$, and $R^8$ is independently selected from H and methyl.

In the process of the present invention, the percentage of cobalt oxide in the catalyst is usually in the range 3-6, and the percentage of molybdenum oxide in the catalyst is usually in the range 10-20.

The catalytic reaction of the invention is effected at a temperature in the range 500°-800° C., more usually in the range 650°-800° C. Contact times can be adjusted suitably in accordance with the temperature used, but are generally in the range from 0.2-10 seconds.

In the present process the molar ratio of the inert diluent to the substrate indane or methyl substituted indane is in the range from 8/1 to 35/1, and this range is usually from 15/1 to 30/1. Suitable diluents include helium, nitrogen, cabon monoxide, carbon dioxide, argon, and steam. No particular advantage is obtained by carrying out the reaction greatly removed from atmospheric pressure, and absolute pressures of from 10 to 30 psi are convenient, although higher and lower pressures can be employed.

While U.S. Pat. No. 3,456,026 discloses the sulfur dehydrogenation of ethyl benzene to styrene, butane to butadiene and butane to butadiene, and states that the process is applicable to compounds containing 2-20 carbon atoms that contain adjacent carbon atoms containing at least one hydrogen atom and names a large number of specific compounds in this category, this reference does not suggest the use of sulfur dehydrogenation in any fused ring compound. In this reference the catalysts actually employed or specifically suggested are alumina of low surface area, a calcium nickel phosphate, aluminum phosphate, and silica containing sodium oxide and calcium oxide.

In the process of the present invention, the particular catalyst used in the present invention as herein before disclosed is capable of yielding, and does yield, exceptionally high conversions of the starting material indanes to the desired product. These catalysts are not suggested by the reference, although this reference generally discloses the utility of oxides of about half of the metals of the periodic table, in addition to silicon carbide, carbon, and so forth.

As will be seen from the specific examples, a catalyst of the present invention when used in the present process is exceptional. For instance, it will be seen that a catalyst containing nickel and molybdenum oxides on alumina is not nearly so effective as the catalyst used in the present invention, even though nickel and cobalt are often considered to be very closely related oxides and are contiguous members of Group VIII of the Periodic Table.

In the following illustrative specific examples, 20 cc of the granular catalyst was in a fixed bed 20 cc stainless steel tubular reactor (a tube 1.25 cm. inside diameter) equipped with a thermocouple well. The catalyst was heated to operating temperature under nitrogen. Both the hydrocarbon substrate and sulfur were fed to the reactor by passing nitrogen through saturators containing the liquid feeds and kept at elevated temperatures. Mass flow controllers were used to regulate the gas flows. Reactor pressure was essentially atmospheric.

The liquid products were collected in two ice cooled $CCl_4$ scrubbers and the gaseous products in a 250 cc gas gun. Both liquid and gas products were analyzed by gas chromatograph.

EXAMPLE 1

(Comparative)

In this example the catalyst was alumina which had been heat treated at 1100° C. for two hours to lower its surface area from 204 to 59.6 m²/gm. The ratios in the feed were 1 mole indane/2 atoms S/26 moles $N_2$. The reaction temperature was 601° C. and the contact time was 0.96 seconds. In this and all examples in calculating contact time an atoms of sulfur was arbitrarily considered to have the same volume as 1 mole of indane. In this run the conversion of the indane was 97.3 percent and the yield of indene was 46.4 percent.

EXAMPLE 2

The catalyst precursor used in this example consisted of 3.5 weight percent CoO and 12.5 weight percent $MoO_3$ on an alumina support (84 percent.) The precursor had a surface area (BET method) of 236 sq. meters/gram. Before use as the catalyst in this example a portion of the precursor was reduced in surface area to 56.4 m²/gm. by heating for 2 hours at 900° C. The temperature of the reaction was 701° C., the contact time was 1.64 seconds, and the ratios were 1 mole indane/1 atom S/26 moles $N_2$. The indane conversion was 100 percent and yield of indene was 89.3 percent.

It will be noted that comparative Example 1 gave a much higher conversion to unwanted products other than indene, even though the conditions were much milder. Both catalysts had about the same surface area.

EXAMPLE 3

In this example the same catalyst precursor was heat treated at 1100° C. for 2 hours to reduce the catalyst area to 3.2 m²/gm before use as the catalyst in this example. The reaction temperature was 726° C., the contact time was 1.60 seconds, and ratios of the feed components to the reaction tube were the same as in Example 2. The indane conversion was 95.8 percent and the yield of indene was 92.9 percent.

EXAMPLE 4

(Comparative)

The catalyst precursor used in this example consisted of 4.0 weight percent NiO and 14.0 weight percent $MoO_3$ on an alumina support (82 percent.) The precursor had a surface area (BET method) of 230 sg. meters/gram. Before use as the catalyst in this example a portion of the precursor was reduced in surface area to 5.90 m²/gm by heating for 2 hours at 1100° C. The temperature of the reaction was 700° C., the contact time was 1.64 seconds, and the ratios were 1 mole indane/1 atom S/26 moles $N_2$. The indane conversion was 98.3 percent and yield of indene was 70.8 percent.

It will be noted that when compared to Examples 2 and 3, this catalyst is not nearly as effective as the catalyst of the invention process, even though nickel and cobalt are often considered to be chemically similar, and are of course contiguous members of Group VIII of the Periodic Table.

EXAMPLES 5-7

In the following examples the ratio of the moles of $N_2$ to moles of indane in the feed was 22/1 and the ratio of S atoms to moles of indane was varied, as shown in the second column of Table 1. The table shows the reaction conditions. The catalyst was made by heating the precursor described in Example 2 for 2 hours at 1100° C. This treatment produced a catalyst having a surface are of 3.2 m²/gm.

TABLE 1

| | | Effect of S/Indane Ratio (Atoms of S/Mole of Indane) | | | |
|---|---|---|---|---|---|
| Example | Ratio S/Indane | Reaction Temp. °C. | Contact Time Seconds | Percent Conversion | Percent Indane Yield |
| 5 | 0.5/1 | 676 | 1.71 | 83.3 | 65.9 |
| 6 | 1/1 | 686 | 1.66 | 93.8 | 87.8 |
| 7 | 2.5/1 | 686 | 1.68 | 97.3 | 71.2 |
| 8 | 8/1 | 687 | 1.64 | 94.9 | 50.5 |

The products of the invention, indene or the methyl substituted indenes have varied uses. All of the products of the present invention are polymerizable to solid thermoplastic polymers useful to mold utilitarian objects, such as tumblers, plates, containers, etc.

The polymerization can be effected using $BF_3$, $TiCl_4$, $SnCl_4$, or $SnCl_5$ as catalysts at low temperatures by the method of Plyusnin, Babin and Chertkova in Zh. Prikl. Khim. 29, 1070 (1956.)

As will be evident to those skilled in the art various modifications of this invention can be made or followed in the light of the foregoing disclosure and discussion without departing from the spirit and scope of the disclosure or from the scope of the claims.

We claim:

1. A process for the catalytic reaction of sulfur and an indane compound having the formula:

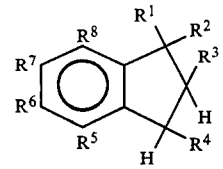

in the vapor phase in the presence of an inert gaseous or vapor diluent to produce

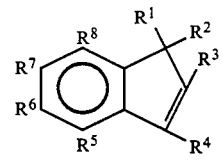

by contacting the reaction mixture with a solid catalyst having 1-10 weight percent CoO, 5-40 weight percent $MoO_3$, the balance of the catalyst being an alumina support, wherein the catalyst contains a Co to Mo ratio in the range from 1/2.5 to 1/6 and wherein the catalyst has a surface area of less than 80 m²/gm, the ratio of atoms of sulfur to moles of indane compound in the feed being in the range from 0.8 to 2, and wherein each of $R^1$, $R^2$, $R^3$, $R^4$, $R^5$, $R^6$, $R^7$, and $R^8$ is independently selected from H and methyl.

2. A process of claim 1 wherein the reaction temperature is in the range from 500°-800° C.

3. A process of claim 1 wherein said indane compound is indane.

4. A process of claim 2 wherein said indane compound is indane.

* * * * *